United States Patent [19]

Porteous et al.

[11] Patent Number: 4,772,324

[45] Date of Patent: * Sep. 20, 1988

[54] HYDROCOLLID GEL BASED DENTAL IMPRESSION COMPOSITION

[75] Inventors: Don D. Porteous, Los Angeles; Ornan Valle, Culver City, both of Calif.

[73] Assignee: Van R Dental Products, Inc., Los Angeles, Calif.

[*] Notice: The portion of the term of this patent subsequent to Mar. 10, 2004 has been disclaimed.

[21] Appl. No.: 865,153

[22] Filed: May 20, 1986

[51] Int. Cl.$^4$ .............................................. A61K 6/10
[52] U.S. Cl. .................................. 106/35; 106/38.51; 106/208; 106/209; 264/16; 264/DIG. 30; 433/214; 523/109
[58] Field of Search ............... 523/109; 106/35, 208, 106/209, 38.51; 433/214; 264/16, DIG. 30

[56] References Cited

U.S. PATENT DOCUMENTS

| | | | |
|---|---|---|---|
| 2,298,835 | 10/1942 | Noyes | 523/109 |
| 4,075,316 | 2/1978 | Cordon | 424/49 |
| 4,187,287 | 2/1980 | Schreiber et al. | 424/49 |
| 4,242,239 | 12/1980 | Kessler et al. | 523/109 |
| 4,394,172 | 7/1983 | Scheuble et al. | 106/35 |
| 4,648,906 | 3/1987 | Porteous et al. | 106/35 |

FOREIGN PATENT DOCUMENTS 260089 10/1967 U.S.S.R.

*Primary Examiner*—Paul Lieberman
*Assistant Examiner*—Linda D. Skaling
*Attorney, Agent, or Firm*—Louis J. Bachand

[57] ABSTRACT

A dental impression composition is provided which has relatively lower water content for higher tensile and gel strengths, and an effective amount of dipopylene gylcol to offset the reduced amount of water and provide workability in the composition at storage tempering temperatures of as little as 130° F.

11 Claims, No Drawings

HYDROCOLLID GEL BASED DENTAL IMPRESSION COMPOSITION

TECHNICAL FIELD

The present invention has to do with dental impression materials, namely reversible hydrocolloid gel compositions having improved strength and working properties by virtue of the use of dipropylene glycol in the compositions in lieu of a portion of the water normally used to form the gels.

BACKGROUND OF THE INVENTION

In dental practice the professional uses impression materials to obtain impressions of teeth which are then used to mold bridges, crowns and inlays, or other prosthesis. Precision of impression molds is a paramount consideration for comfort and success of the prosthesis. Realizing precision of impression is dependent on obtaining a good impression in the first place, and this requires workability in the impression material used, and maintaining the good impression and this requires high gel strength and tensile strength in the gelled impression composition during removal from the teeth and through use in the forming the plaster from which the prosthesis is to be made.

Many dentists prefer the use of reversible hydrocolloid gels as impression compositions which are unparalleled for accuracy. These gels are obtained by mixing water and a gel base such as agar-agar, and tempering the gel in a conditioning bath until used.

The following patents relate to reversible hydrocolloid gel impression materials, and have been considered in preparing this application: U.S. Pat. No. 2,021,059 to Harrison; U.S. Pat. No. 2,089,552 to Harrison; and, U.S. Pat. No. 2,234,583 to Preble. The first two of these patents teach the use of glycerol in hydrocolloid compositions, but such systems require a higher temperature tempering bath to avoid loss of workability, and thus a pre-application conditioning step, while the last of these patents teaches that an increase in strength of reversible hydrocolloid gel materials is realized by the use of borates, but such systems are lumpy, too viscous for ready workability, usability under patient tolerable temperature conditions, and may well lack good stone set.

SUMMARY OF THE INVENTION

It is an object of the present invention to provide an improved dental impression composition. It is another object to provide a dental impression material which is improved in gel strength and tensile strength, is less volatile so as to have reduced evaporation, and which has improved workability for easier and more accurate impression taking. It is yet another object to provide a dental impression material which may be maintained in a tempering bath at less than 150° F., e.g about 130° F. rather than the usual 150° F. while maintaining superior workability, for direct application to the patient without an extra cooling step.

These and other objects of the invention to become apparent hereinafter are realized in accordance with the invention in the low temperature tempering, high gel strength, high tensile strength dental impression composition consisting essentially of a reversible hydrocolloid gel forming base and an aqueous reagent in an amount sufficient to form a reversible gel with the base, the reagent comprising from 50 to 95% by weight water and the balance dipropylene glycol.

In particular embodiments, the gel forming base is agar-agar; the composition is free of glycerine; the weight ratio of aqueous reagent to gel forming base is between 8 and 12; and there may be included also an acid buffering compound in effective amount, e.g. a borate radical donor compound in acid buffering amount in the composition, such as an alkaline earth metal borate, particularly zinc borate.

In a preferred embodiment of the invention, there is provided a low temperature tempering, high gel strength, high tensile strength dental impression composition consisting essentially of a reversible hydrocolloid gel forming base and an aqueous reagent in an amount equal to the amount of water sufficient to form a reversible gel with the base, the reagent comprising water in relatively reduced amount to increase the gel strength and the tensile strength of the gel and the balance dipropylene glycol in an amount maintaining workability in the impression material with the reduced amount of water.

In this as in other embodiments of the invention preferably the weight ratio of dipropylene glycol to gel base in the composition is between 1.5 and 5.0; the gel forming base is agar-agar; the composition is free of glycerine; the weight ratio of aqueous reagent to gel forming base is between 8 and 12; there is also present an acid buffering compound in effective amount; the acid buffering compound is a borate radical donor compound present in acid buffering amount in the composition; the borate radical donor compound is an alkaline earth metal borate; the alkaline earth metal borate compound is zinc borate; and the zinc borate is present in an amount of 5 to 20% by weight based on the weight of the gel base.

In a highly particularly preferred embodiment of the invention there is provided a low temperature tempering, high gel strength dental impression composition consisting essentially of from 8 to 12 parts agar-agar, from 60 to 80 parts water, from 15 to 30 parts dipropylene glycol, and from 0.3 to 2.5 parts of borate radical donor compound, per 100 parts by weight, wherein the borate radical donor compound is zinc borate.

The invention further contemplates the method of increasing the gel strength and tensile strength of reversible hydrocolloid compositions comprising a reversible hydrocolloid forming base and a predetermined weight amount of water sufficient to form a gel with the base, including omitting from 10 to 35% of the predetermined amount of water and adding to the composition an amount of dipropylene glycol equal to from 50 to 150% of the water weight amount omitted.

DETAILED DESCRIPTION

As noted above, the present composition includes a reversible hydrocolloid gel forming base and an aqueous reagent. The base is typically agar-agar, but may be any of the gel forming materials known in the art including Irish moss, Iceland moss, etc. The aqueous reagent comprises water and the dipropylene glycol. The reagent typically comprises from 50 to 95% by weight water and the balance dipropylene glycol, with preferred proportions being 65 to 75 weight percent water and conversely 35 to 25 weight percent of the glycol. The aqueous reagent is preferably free or substantially free (less than 5% by weight) of glycerine which has been found to disadvantageous in formulating a composition which is temperable at the lower range of less than 150° F. and preferably about 130 ° F. rather than the typical 150° F.

The aqueous reagent is typically present in an amount of 8 to 12 parts by weight per part of gel forming base, and preferably about 10 parts per part of base, with the weight ratio of dipropylene glycol to gel base in the composition being in the 1.5 to 5 range and preferably about 2.5 to 3.5.

The use of a buffering compound improves the gel life, and for this purpose borate radical compounds have been found highly useful, particularly the alkaline earth borates such as and especially zinc borate in amounts of 5 to 20% by weight based on the weight of the gel base.

The combination of zinc borate and dipropylene glycol with agar-agar gel forming base in the just discussed proportions has been found to provide a uniquely advantageous hydrocolloid dental impression material with nearly ideal properties of gel strength (improved about 30% over glycerine formulas), tensile strength (improved about 30% over glycerine formulas) tempering ability (130° F. vs. 150° F. for glycerine formulas), reduced rate of evaporation, dramatically better texture and workability than glycerine formulas at the cooler temper, and accuracy of impression particularly at undercuts is heightened.

EXAMPLE

A typical composition according to the invention is prepared by placing the following materials in a suitable heated vessel: 140 parts by weight of agar-agar melted in 1050 parts of boiling water; a thickener at 10 parts and dissolved into the agar-agar water mixture; zinc borate at 15 parts predissolved in a minimum amount of water; and 350 parts of dipropylene glycol with flavoring and colorant if desired and the entire mass blended until uniform and then the mixture is put up in small tubes for use by the dentist.

It is noted that the composition contains less than the usual amount of water by about 10 to 35%. This reduced amount of water translates to greater gel strength and greater tensile strength in the set composition. The reduced amount of water makes the composition relatively more viscous, which is useful in obtaining impressions on undercuts and vertical surfaces. Nonetheless the composition exhibits smooth workability, the viscosity is in the nature of thixotropy, and under spatulation, syringing or like forming techniques, the viscosity is a benefit and not a drawback, where the omitted water is replaced by from 50 to 150% of the water weight amount of the dipropylene glycol.

We claim:

1. Low temperature tempering, high gel strength, high tensile strength dental impression composition consisting essentially of a reversible hydrocolloid gel forming base and an aqueous reagent in an amount sufficient to form a reversible gel with said base, said reagent comprising from 50 to 95% by weight water and the balance dipropylene glycol.

2. Low temperature tempering, high gel strength, high tensile strength dental impression composition according to claim 1, in which said gel forming base is agar-agar.

3. Low temperature tempering, high gel strength, high tensile strength dental impression composition according to claim 1, in which said composition is substantially free of glycerine.

4. Low temperature tempering, high gel strength, high tensile strength dental impression composition according to claim 1, in which the weight ratio of aqueous reagent to gel forming base is between 8 and 12.

5. Low temperature tempering, high gel strength, high tensile strength dental impression composition according to claim 1, including also an acid buffering compound in effective amount.

6. Low temperature tempering, high gel strength, high tensile strength dental impression composition consisting essentially of a reversible hydrocolloid gel forming base and an aqueous reagent comprising water sufficient to form a reversible gel with said base, and dipropylene glycol in a weight ratio of dipropylene glyvol to gel base between 1.5 and 5.0.

7. Low temperature tempering, high gel strength, high tensile strength dental impression composition according to claim 6, in which said gel forming base is agar-agar.

8. Low temperature tempering, high gel strength, high tensile strength dental impression composition according to claim 7, in which said composition is free of glycerine.

9. Low temperature tempering, high gel strength, high tensile strength dental impression composition according to claim 7, in which the weight ratio of aqueous reagent to gel forming base is between 8 and 12.

10. Low temperature tempering, high gel strength, high tensile strength dental impression composition according to claim 9, including also an acid buffering compound in effective amount.

11. Low temperature termpering, high gel strength dental impression composition consisting essentially of from 8 to 12 parts agar-agar, from 60 to 80 parts water, from 15 to 30 parts dipropylene glycol, and from 0.3 to 2.5 parts of an acid buffering compound, per 100 parts by weight.

* * * * *